(12) United States Patent
Zhu et al.

(10) Patent No.: US 6,310,479 B1
(45) Date of Patent: Oct. 30, 2001

(54) MAGNETIC RESONANCE PROJECTION IMAGING OF DYNAMIC SUBJECTS

(75) Inventors: Yudong Zhu, Clifton Park; Christopher Judson Hardy, Schenectady, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/378,501

(22) Filed: Aug. 20, 1999

(51) Int. Cl.[7] ........................................... G01V 3/00
(52) U.S. Cl. ................................................. 324/312
(58) Field of Search ........................ 324/312, 309; 600/413

(56) References Cited

U.S. PATENT DOCUMENTS

| | | | |
|---|---|---|---|
| 4,952,877 | 8/1990 | Stormont et al. | 324/312 |
| 4,992,736 | 2/1991 | Stormont et al. | 324/309 |
| 5,000,182 | * 3/1991 | Hinks | 600/413 |
| 5,285,158 | * 2/1994 | Mistretta et al. | 324/309 |
| 5,339,035 | 8/1994 | Schneider et al. | 324/309 |

* cited by examiner

*Primary Examiner*—Jay Patidar
*Assistant Examiner*—Dixomara Vargas
(74) *Attorney, Agent, or Firm*—Jean K. Testa; Donald S. Ingraham (57) ABSTRACT

An MRI system performs a cardiac gated scan of a moving coronary artery using preparatory pulse sequences and two-dimensional EPI (echo planar imaging) pulse sequences. The preparatory pulse sequence saturates spin magnetization in regions surrounding a slice which contains the coronary artery at one point in time during each cardiac cycle. The EPI imaging pulse sequence is performed later in the cardiac cycle after the coronary artery has moved and a two-dimensional image is reconstructed by projecting NMR signals from a volume within which the coronary artery moves during the cardiac cycle.

24 Claims, 7 Drawing Sheets

MAGNETIC RESONANCE PROJECTION IMAGING OF DYNAMIC SUBJECTS

BACKGROUND OF THE INVENTION

This invention relates to magnetic resonance imaging (MRI) methods and systems and, more particularly, to the imaging of moving three-dimensional subjects such as coronary arteries.

When a substance such as human tissue is subjected to a uniform magnetic field (polarizing field $B_0$), the individual magnetic moments of the nuclear spins in the tissue attempt to align with this polarizing field along the z-axis of a Cartesian coordinate system and consequently precess about the polarizing field in random order at their characteristic Larmor frequency. If the substance, or tissue, is subjected to an excitation magnetic field (excitation field $B_1$) which is in the x-y plane and which is near the Larmor frequency, the net aligned moment $M_z$ may be rotated, or "tipped", into the x-y plane to produce a net transverse magnetic moment $M_t$. A signal is emitted by the excited spins after the excitation field $B_1$ is terminated, and may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR (nuclear magnetic resonance) signals are digitized and processed to reconstruct the image using one of many well known reconstruction techniques.

The imaging of three-dimensional subjects can be accomplished using either two-dimensional (2D) or three-dimensional (3D) MR imaging methods. The acquisition of a 3D image requires the repeated performance of a 3D imaging pulse sequence during which two separate phase encoding gradients are stepped through a large number of values. To acquire a high resolution 3D image, more phase encoding steps are required and this causes the scan to become too lengthy for many clinical applications.

A high resolution 2D MR image can be acquired in a much shorter scan time. To examine a three-dimensional subject therefore, it is common practice to acquire one or more 2D slice images that have been precisely located with respect to the subject. Precise location may be accomplished by acquiring a low resolution MR image and using an interactive display to graphically prescribe the precise location of a subsequent high resolution 2D scan. This strategy can be used successfully when the subject is stationary and the region of interest can be located in a 2D slice image.

In many clinical applications, high resolution images of moving 3D subjects must be acquired. One such application is imaging of the coronary arteries, three-dimensional objects that move substantially during the cardiac cycle. It is sometimes possible to position a 2D "slice" acquisition to capture a portion of the subject coronary artery in the 2D imaging plane at some point in the cardiac cycle, but it may not be possible to capture the same portion at other cardiac phases because the vessels move in and out of the 2D slice constantly as the heart beats. In addition, imaging all of the coronary artery segments of interest may require many separate 2D image acquisitions.

SUMMARY OF THE INVENTION

A method and system for imaging a 3D moving subject includes altering differently the longitudinal magnetization of spins located inside and outside a confined region of a 3D moving subject using a preparation pulse sequence, acquiring 2D projection views of the moving subject from a specified projection direction, and reconstructing a 2D projection image from the acquired data. Rather than imaging a fixed 2D or 3D region of space, the spins in the confined region of the moving subject are transversely excited, and even when the spins move into a different region of space, they produce an NMR signal that is acquired by the projection acquisitions. Spins outside the confined region contribute minimally to the acquired NMR signal due to the application of the preparatory pulse sequence.

DESCRIPTION OF THE PREFERRED EMBODIMENT

Figure 1:
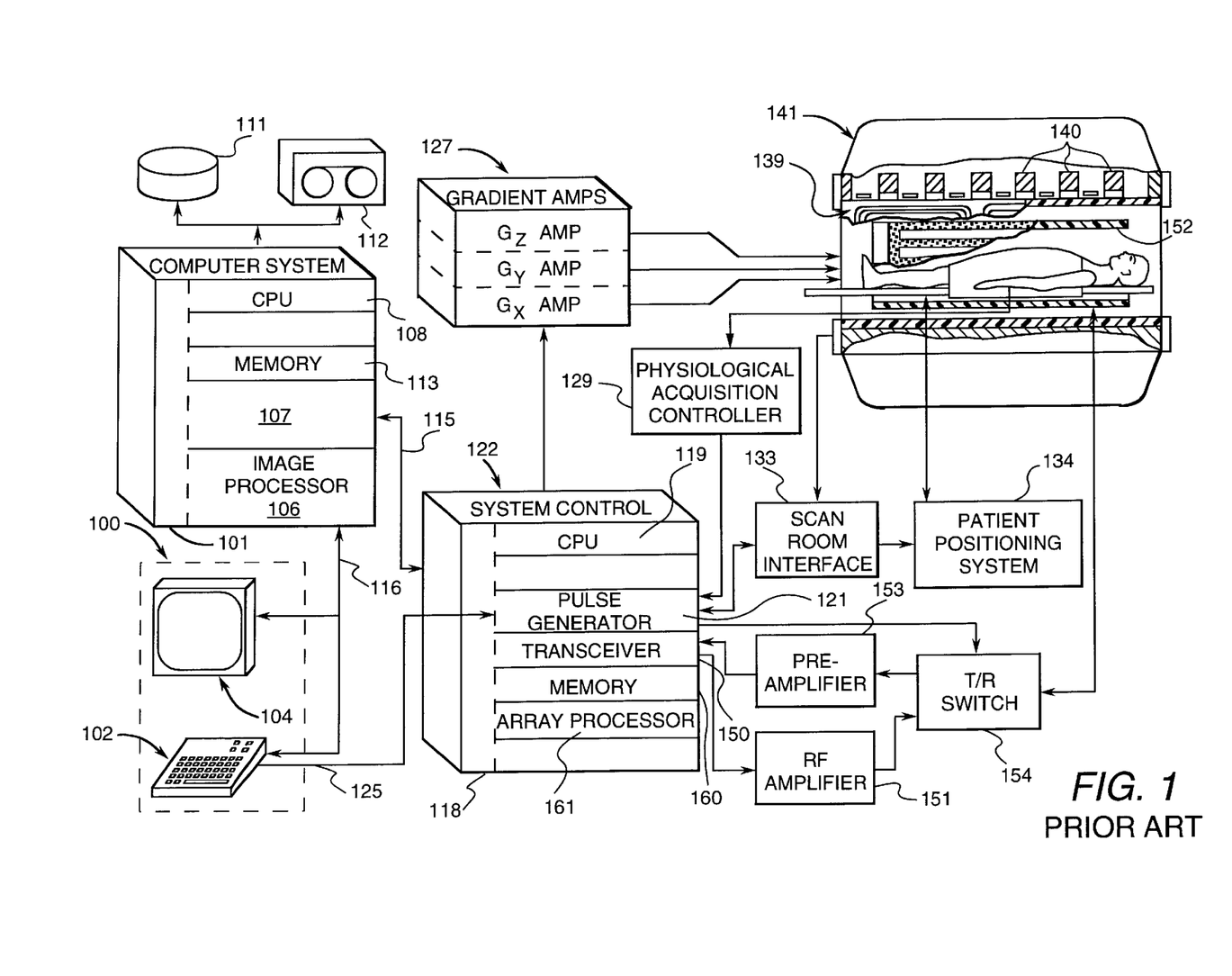
FIG. 1 is a block diagram of an MRI system employing the invention.

FIG. 1 shows the major components of a preferred MRI system which incorporates the invention. Operation of the system is controlled from an operator console 100 which includes a keyboard and control panel 102 and a display screen 104. Console 100 communicates through a link 116 with a separate computer system 107 that enables an operator to control the production and display of images on screen 104. Computer system 107 includes a number of modules which communicate with each other through a backplane 101. These modules include an image processor 106, a CPU (central processing unit) 108 and a memory 113, known in the art as a frame buffer, for storing image data arrays. Computer system 107 is linked to a disk storage 111 and a tape drive 112 for storing of image data and programs, and communicates with a separate system control 122 through a high speed serial link 115.

System control 122 includes a set of modules coupled together by a backplane 118. These modules include a CPU 119 and a pulse generator 121 coupled to operator console 100 through a serial link 125. System control 122 receives, through line 125, commands from the operator that indicate the scan sequence to be performed.

Pulse generator module 121 operates the system components to carry out the desired scan sequence, producing data which designate the timing, strength and shape of the RF pulses to be produced, and the timing and length of the data acquisition window. Pulse generator module 121 is coupled to a set of gradient amplifiers 127 to designate the timing and shape of the gradient pulses to be produced during the scan. Pulse generator module 121 also receives patient data from a physiological acquisition controller 129 that receives signals from various sensors attached to the patient, such as ECG (electrocardiograph) signals from electrodes that synchronize operation of pulse generator module 121 with the cardiac cycle of the patient. Pulse generator module 121 is coupled to a scan room interface circuit 133 which also receives signals from various sensors associated with the condition of the patient and the magnet system. Patient positioning system 134 receives, through scan room interface circuit 133, commands to move the patient to the desired position for the scan.

The gradient waveforms produced by pulse generator module 121 are applied to gradient amplifier system 127 comprised of $G_x$, $G_y$ and $G_z$ amplifiers. Each gradient amplifier excites a corresponding gradient coil in an assembly 139 to produce the magnetic field gradients used for position encoding acquired signals. Gradient coil assembly 139 forms part of a magnet assembly 141 which includes a polarizing magnet 140 and a wholebody RF coil 152. A transceiver module 150 in system control 122 produces pulses which are amplified by an RF amplifier 151 and supplied to RF coil 152 by a transmit/receive switch 154. The resulting signals radiated by the excited nuclei in the patient may be sensed by the same RF coil 152 and supplied through transmit/receive switch 154 to a preamplifier 153. The amplified NMR signals are demodulated, filtered, and digitized in the receiver section of transceiver 150. Transmit/receive switch 154 is controlled by a signal from pulse generator module 121 to electrically couple RF amplifier 151 to coil 152 during the transmit mode and to preamplifier 153 during the receive mode. Transmit/receive switch 154 also enables a separate RF coil (for example, a head coil or surface coil) to be used in either the transmit or receive mode.

The NMR signals picked up by RF coil 152 are digitized by transceiver module 150 and transferred to a memory module 160 in system control 122. When the scan is completed and an entire array of data has been acquired in memory module 160, an array processor 161 operates to Fourier transform the data into an array of image data which are conveyed through serial link 115 to computer system 107 for storage in disk memory 111. In response to commands received from operator console 100, the image data may be archived on tape drive 112, or may be further processed by image processor 106 and conveyed to operator console 100 for presentation on display screen 104.

For a more detailed description of transceiver 150, reference is made to Stormont et al. U.S. Pat. No. 4,952,877, issued Aug. 28, 1990 and U.S. Pat. No. 4,992,736, issued Feb. 12, 1991, both of which are assigned to the instant assignee and incorporated herein by reference.

The moving object to be imaged in the preferred embodiment of the invention is a coronary artery of a human subject. The coronary arteries are distributed on the surface of the heart and move in space as the heart beats. The invention is practiced in this application by performing a preparation pulse sequence at a preselected time during each cardiac cycle and then performing a series of imaging pulse sequences at successive phases of the cardiac cycle. The preparatory pulse sequence defines a slice of spins that includes the coronary artery to be examined at the preselected time, and the imaging pulse sequences define a volume that includes the coronary artery at all phases of the cardiac cycle.

Figure 2:
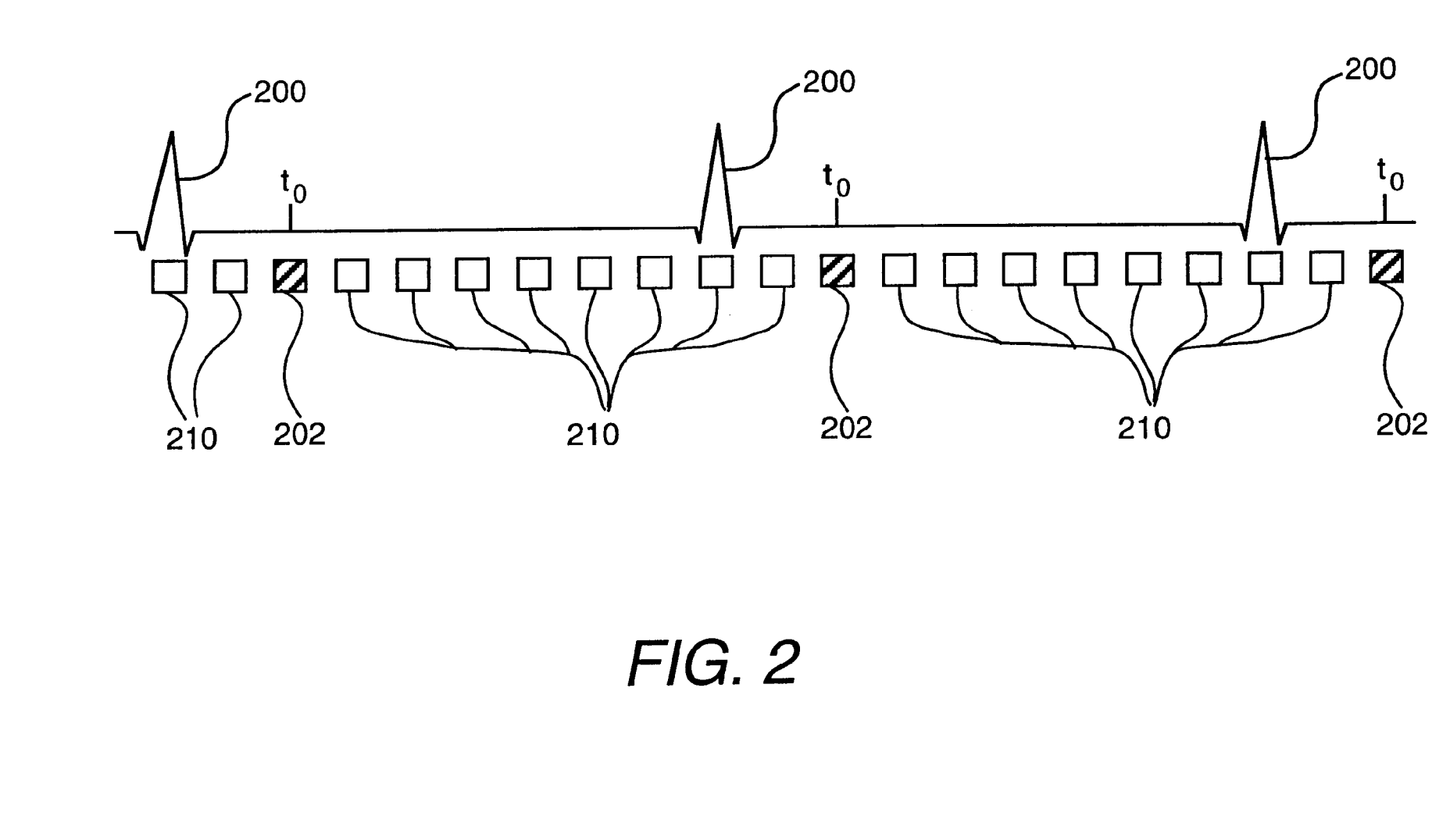
FIG. 2 Is graphic representation of a preferred cardiac-triggered image acquisition procedure using the MRI system of FIG. 1.
Figure 3:
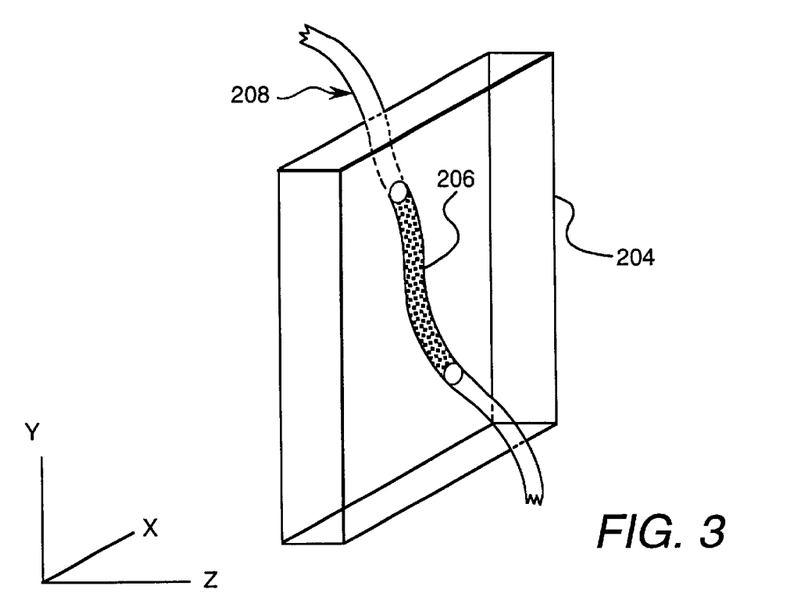
FIG. 3 is a pictorial representation of a slice containing a coronary artery to be imaged at one cardiac phase.

The data acquisition is synchronized with the beat of the patient's heart by an ECG signal that produces cardiac gating signals for pulse generator module 121 after the peak of R-waves 200, as shown in FIG. 2. At a preselected time to after each cardiac gating signal, a preparation pulse sequence 202 is performed by the MRI system. This preparation pulse sequence defines a selected region which contains the coronary artery to be imaged. As shown in FIG. 3, this selected region may be a planar section or "slice" 204 which includes a segment 206 of a coronary artery 208. During subsequent phases of the cardiac cycle a series of imaging pulse sequences 210 are performed by the MRI system. These imaging pulse sequences define a volume 212, shown in FIG. 4, which is larger than slice 204 and which includes coronary artery segment 206 at any of its spatial locations during the cardiac cycle. These imaging pulse sequences acquire NMR data from which images may be reconstructed. Each image is a projection of NMR signals from volume 212 as seen along a projection vector 214 and this projection can be acquired from any chosen direction. Thus even though coronary artery segment 206 moves in and out of slice 204 during the cardiac cycle, each imaging pulse sequence acquires NMR signals from the entire segment 206.

Many different imaging pulse sequences may be employed to practice the invention. The particular sequence chosen will depend on the particular clinical application. In a preferred embodiment a multi-shot, interleaved, echo planar imaging (EPI) pulse sequence is used.

Figure 4:
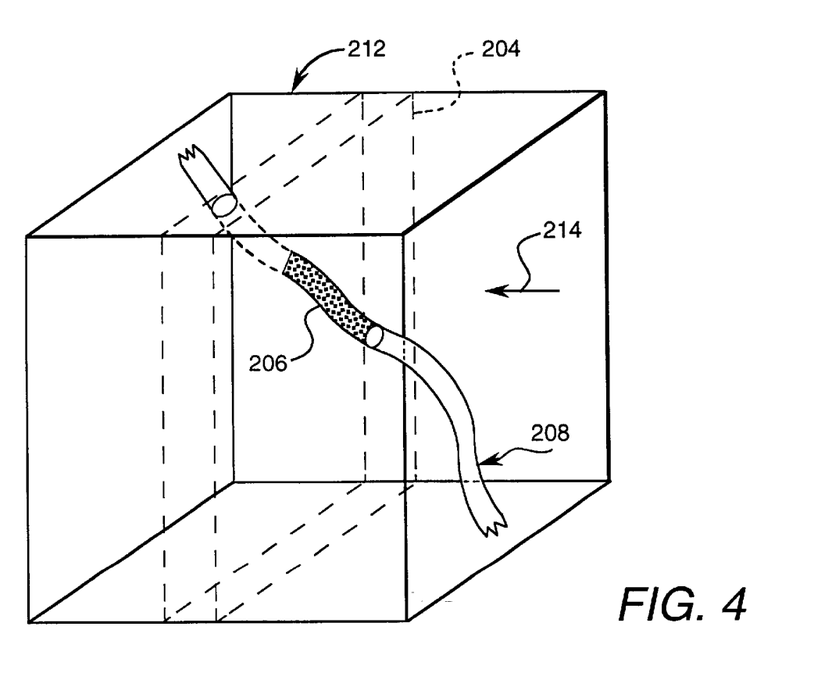
FIG. 4 is a pictorial representation of the same coronary artery of FIG. 3 at another phase of the cardiac cycle.
Figure 5:
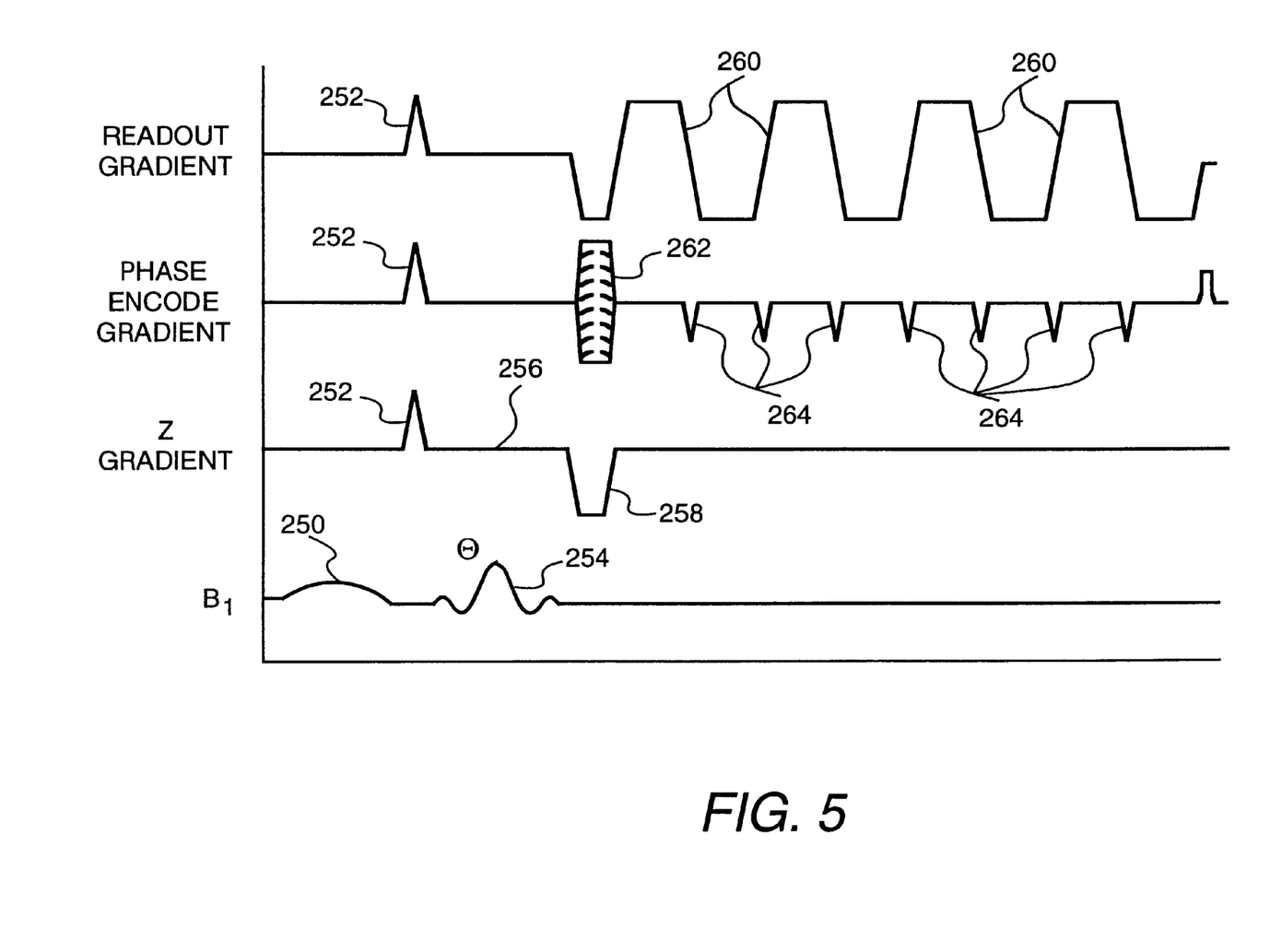
FIG. 5 is a graphic representation of a preferred imaging pulse sequence used in the scan of FIG. 2.

In FIG. 5, the EPI pulse sequence is shown to include a spectrally selective RF saturation pulse 250 which is tuned to saturate fat spins. The resulting transverse magnetization is dephased by magnetic field gradient pulses 252 applied along all three orthogonal gradient axes. This is followed by a selective RF excitation pulse 254 having a flip angle θ which is produced in the presence of a Z-axis magnetic field gradient pulse 256. The frequency content of RF pulse 254 and the amplitude of Z-axis gradient pulse 256 are chosen such that the entire volume 212 (FIG. 4) of spins is excited. Ideally, these values are prescribed such that the size of volume 212 along the Z-axis is slightly larger than the Z-axis movement of coronary artery segment 206 during the entire cardiac cycle. The resulting transverse magnetization produced throughout volume 212 is then rephased by a negative Z-axis gradient pulse 258, shown in FIG. 5. The area under gradient pulse 258 is calculated to have a value different from that needed to exactly rephase the spin magnetization across the entire volume 212. This additional magnetic field gradient creates a small phase roll in the NMR signals produced by spins disposed along the projection direction 214, causing suppression of unwanted signals across volume 212.

A readout gradient which alternates in polarity to form a series of positive and negative readout gradient lobes 260 is produced and a corresponding series of NMR echo signals (not shown) are acquired and stored. A prephaser gradient pulse 262 is applied in the phase encoding direction and a series of phase encoding gradient pulses 264 are applied prior to each positive and negative readout gradient lobe 260 to uniquely phase encode each corresponding NMR echo signal. As is well known in the art, the EPI pulse sequence is repeated (or "shot") a number of times, and prephaser gradient 262 is stepped through a corresponding set of values such that all of $k_y$ space is sampled in an interleaved manner. In a preferred embodiment, anywhere from 1 to 8 NMR signals, or views, are acquired during each EPI shot, and from 16 to 128 shots are acquired during the scan. Each EPI shot is acquired at the same cardiac phase during each of a corresponding number of successive cardiac cycles, and the resulting two-dimensional array of k-space data is Fourier transformed along the readout and phase-encoding axes to produce a two-dimensional image. This two-dimensional image is a projection along the Z-axis of all the spin signals in volume 212 (FIG. 4). As a result, the NMR signals from all of the coronary artery segment 206 are projected onto this 2D image regardless of their location within volume 212 at the particular moment in the cardiac cycle that the NMR signals are required.

If the imaging pulse sequence 210 (FIG. 2) is employed alone, the projection along the Z-axis through the entire volume 212 will include strong NMR signals from spins throughout the volume. Such signals may obscure vessel segment 206 unless they are suppressed. The function of the preparation pulse sequence 202 of FIG. 2 is to suppress the NMR signals from these other spins so that the clinically important coronary artery segment 206 can be clearly seen in the projected image.

Figure 6:
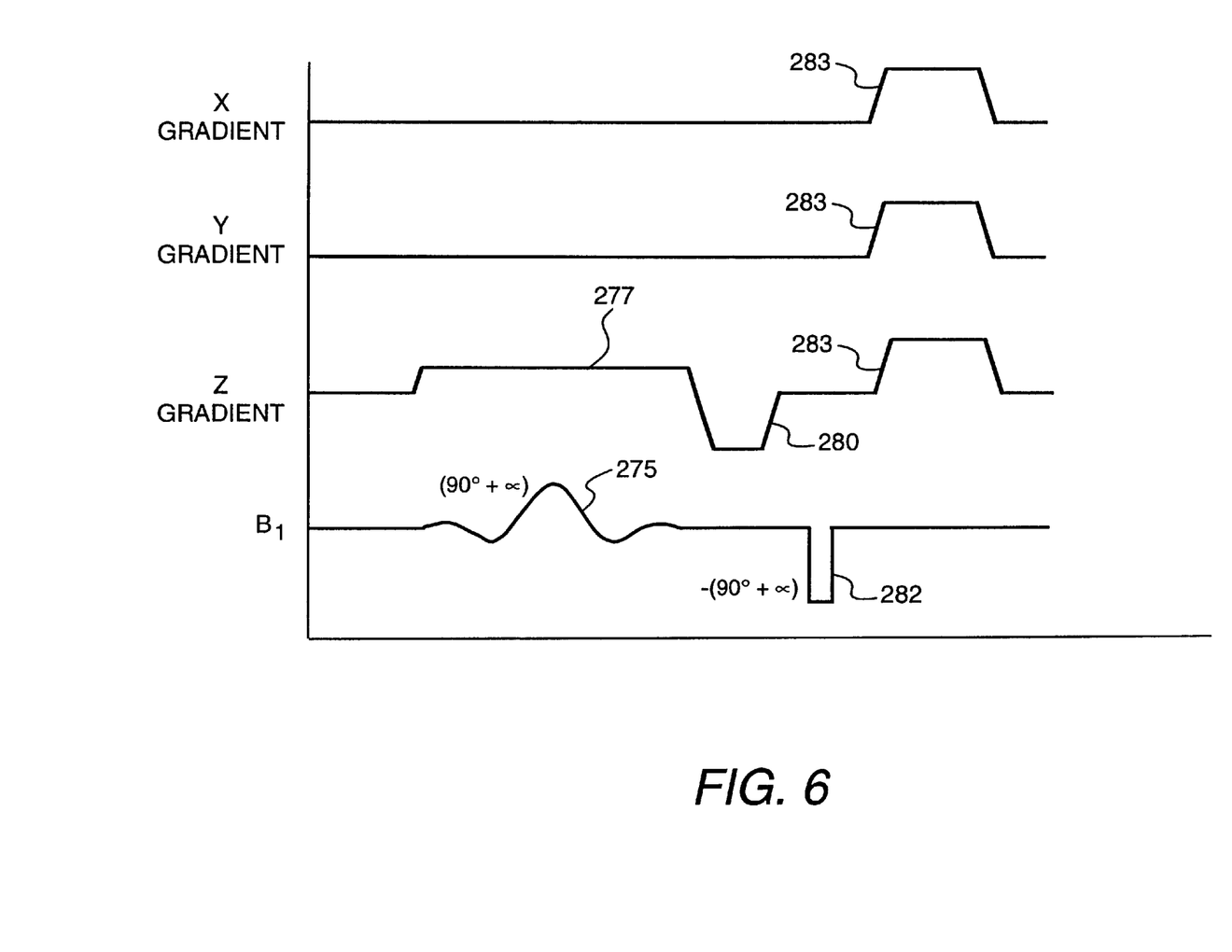
FIG. 6 is a graphic representation of a preferred preparation pulse sequence used in the scan of FIG. 2.

Referring particularly to FIGS. 4 and 6, the preferred embodiment of the preparation pulse sequence 202 (FIG. 2) functions to saturate spin magnetization throughout the region of suppression and includes application of a selective RF excitation pulse 275 produced in the presence of a slice-select gradient pulse 277 directed along the Z axis. The RF excitation pulse 275 has a frequency content and amplitude selected to produce a flip-angle of (90+$\alpha$) degrees in the spins located in slice 204. This transverse magnetization is rephased by a negative rephasing gradient pulse 280 directed along the Z axis.

A non-selective RF excitation pulse 282 is then produced to tip the spin magnetization throughout the entire volume by a flip angle of negative (90+$\alpha$) degrees. This tips the spin magnetization in slice 204 back to the longitudinal Z-axis and saturates the remaining spin magnetization on either side of slice 204. Spoiler gradient pulses 283 are applied immediately thereafter to dephase the transverse magnetization. As a result, only the spins located in slice 204 at time $t_o$ (FIG. 2) will have significant longitudinal magnetization when the subsequent imaging pulse sequences 210 (FIG. 2) are performed. Spins outside slice 204 are substantially saturated and do not produce a strong NMR signal in response to the imaging pulse sequences.

There are many variations in the preparation pulse sequence. For example, the order of the selective RF pulse 275, and its associated gradient pulses 277 and 280 and non-selective RF pulse 282 may be reversed. Two separate selective RF excitation pulses that saturate spins on both sides of slice 204 may be used, or a single selective RF excitation pulse that simultaneously saturates spins on both sides of slice 204 may be used. The choice of method used depends to some extent on the thickness of slice 204 and the capabilities of the particular MRI system. To accommodate the curvature of coronary arteries, the preparation pulse sequence 202 may be applied multiple times to define a plurality of slices which together define a volume that includes the arteries of interest.

The saturated spins outside slice 204 recover their longitudinal magnetization at a rate determined by their $T_1$ relaxation time. The value of alpha for the RF excitation pulses 275 and 282 may be chosen such that the partially recovered longitudinal magnetization at one of the instants of image data acquisition 210 (FIG. 2) contributes minimally to the NMR signal. It should be apparent that this method of suppressing signal from spins located outside slice 204 depends on the $T_1$ (or NMR relaxation time) of the spins and the timing of the image acquisition. Referring to FIG. 2, for example, alpha can be selected such that optimal signal suppression is obtained with one of the imaging pulse sequences 210. However, potentially obscuring signals may still be present with the other imaging pulse sequences 210. This may not be a problem if it is not necessary to see coronary artery segment 206 clearly at all cardiac phases. On the other hand, if this is a problem, the value of alpha can also be changed during the scan to acquire optimally suppressed NMR data at other cardiac phases. For example, the central kspace views for each cardiac phase image may be acquired with an optimum alpha suppression, and the peripheral k-space views may be acquired with less than optimal suppression.

A number of additional measures can be taken to further suppress the signal from spins outside slice 204. One of these methods requires use of another preparation pulse sequence, depicted in FIG. 7. This preparation pulse sequence is identical to that described above and shown in FIG. 6, except the flip angle of selective RF excitation pulse 275 is minus (90–alpha) degrees, and the flip angle of the non-selective RF excitation pulse 282 is minus (90+alpha) degrees. As a result, at the completion of this preparation pulse sequence, the spin magnetization outside slice 204 is saturated and the longitudinal magnetization of the spins inside slice 204 is inverted.

Figure 7:
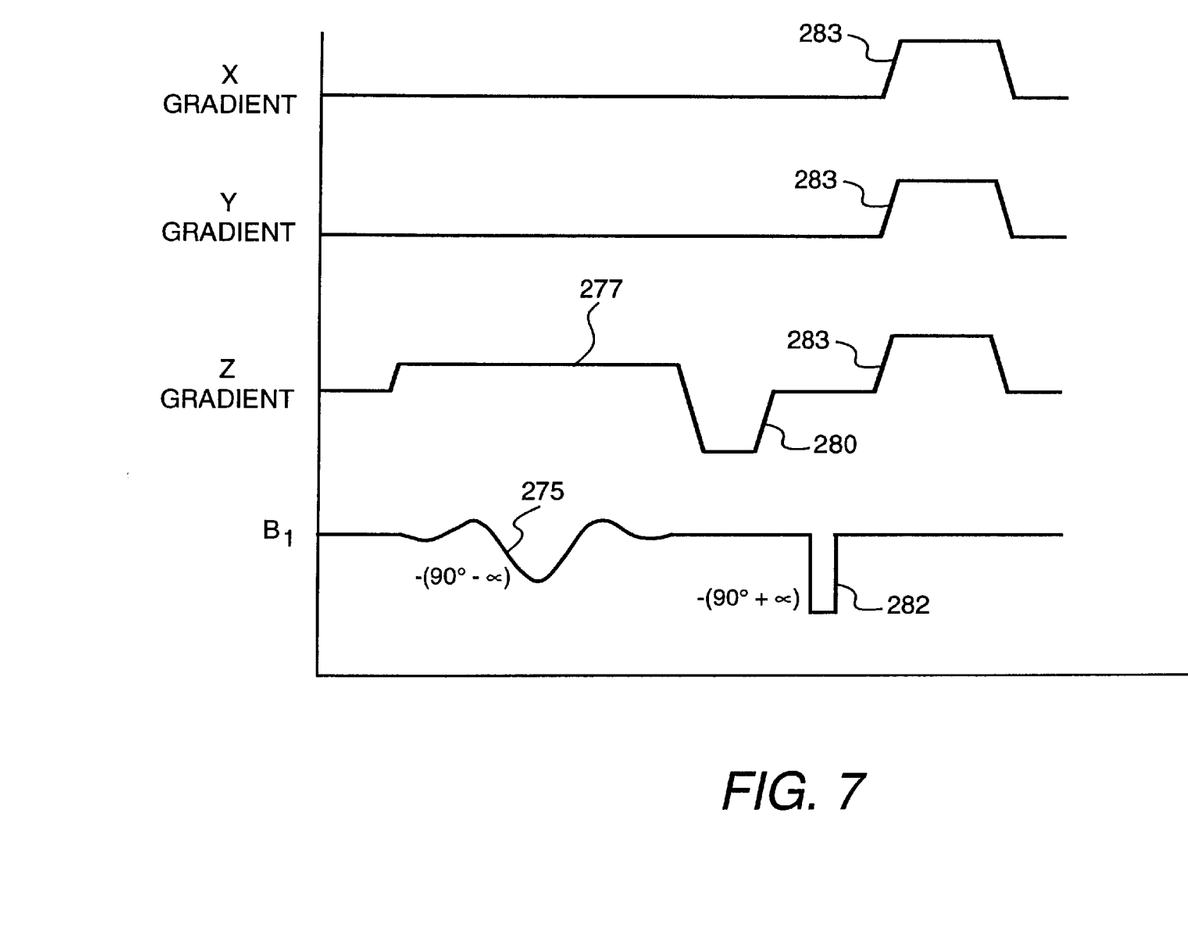
FIG. 7 is a graphic representation of another preparatory pulse sequence that may bused in the scan of FIG. 2.

Suppression of undesired signals is accomplished by using the preparatory pulse sequence of FIG. 6 (i.e. positive longitudinal magnetization) in one cardiac cycle and then acquiring the same image views during the next cardiac cycle using the preparatory pulse sequence of FIG. 7 (i.e. negative longitudinal magnetization). By performing a complex subtraction of the two acquired complex k-space data sets, the signals from in-slice spins will add while the signals from spins outside slice 204 will subtract, or substantially null.

The invention may be used with a wide range of imaging pulse sequences in which a moving object is to be imaged. For example, other EPI pulse sequences may be used as well as spiral k-space sampling pulse sequences. When the vascular system is imaged, contrast agents may be injected into the patient to enhance the NMR signals produced by spins in the blood vessels. In this instance, the scan is timed to acquire NMR data when the contrast bolus flows through the vasculature of interest. When imaging the heart, NMR signals produced by spins in the myocardium may be suppressed by applying a magnetization transfer pulse as part of the preparation pulse sequence 202 (FIG. 2). As disclosed, for example, in Schneider et al. U.S. Pat. No. 5,339,035, issued Aug. 16, 1994 and assigned to the instant assignee, a magnetization transfer pulse is an RF saturation pulse which selectively suppresses the NMR signals from off-resonance spin species.

Figure 8:
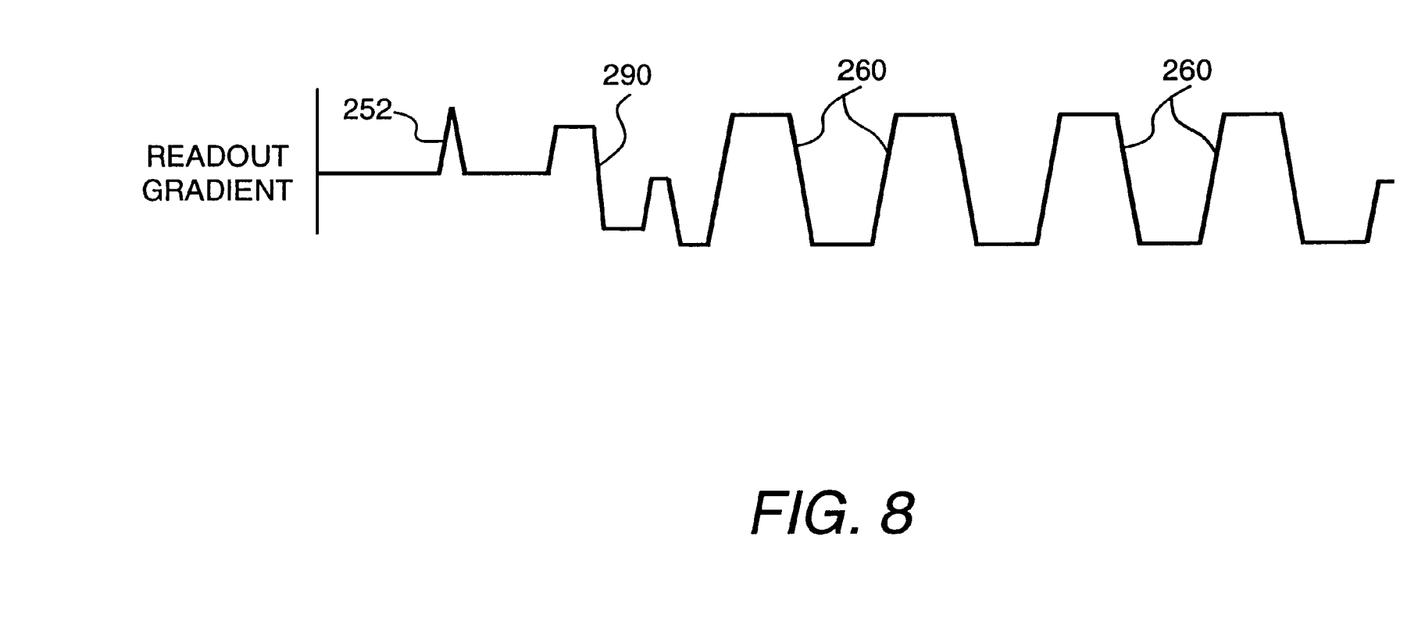
FIG. 8 is a graphic representation of a modification that can be made to the imaging pulse sequence of FIG. 5 to velocity encode the acquired NMR signals.

The invention may also be used to image spin velocity. This is achieved by velocity encoding the transverse magnetization in the imaging pulse sequences 210 (FIG. 2). The velocity encoding imaging pulse sequence is substantially the same as that shown in FIG. 5, except that a bipolar velocity encoding gradient is added to one or more gradient axes after the excitation pulse 254 (FIG. 5) and prior to NMR signal acquisition. Such a bipolar velocity encoding gradient pulse 290 is shown in FIG. 8, applied to the readout gradient axis. Preferably, a phase image is acquired during one set of cardiac cycles with the velocity encoding gradient having a positive first moment M and a similar phase image is acquired during another set of cardiac cycles with a velocity encoding gradient having a negative first moment M. When the two phase images are subtracted, phase shifts due to factors other than spin motion are nulled and a phase difference image is formed. This phase difference image indicates the velocity distribution across the selected object, even though parts of the object may move out of the slice during the scan. This enables a flow and/or deformation analysis to be made without the error introduced by through-plane motion.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for producing an image of a moving object with an MRI system, comprising the steps of:
   a) altering longitudinal magnetization of spins located outside a selected region of spins that includes the moving object, the step of altering longitudinal magnetization of spins comprising:
      i) applying a selective RF excitation pulse to produce a flip angle of (90+α) degrees in the selected region through the moving object; and,
      ii) applying a non-selective RF excitation pulse to alter spins throughout a volume by a flip angle of negative (90+α) degrees;
   b) performing a two-dimensional imaging pulse sequence to acquire NMR signals from spins located in the volume which includes the selected region;
   c) repeating steps a) and b) until sufficient NMR signals are acquired to form an image data set with which an image can be reconstructed; and
   d) reconstructing a two-dimensional image in which the NMR signals produced by spins located in the volume are projected onto the two-dimensional image.

2. The method of claim 1 wherein the step of altering longitudinal magnetization of spins comprises the step of performing a preparatory pulse sequence.

3. The method as recited in claim 1 in which the selected region is a planar section through the moving object.

4. The method as recited in claim 1 in which the selected region is a plurality of planar sections through the moving object.

5. The method as recited in claim 2 in which the selected region is a planar section through the moving object.

6. The method as recited in claim 3 in which steps a), b) and c) are repeated to form a second image data set, the selective RF excitation pulse is applied to establish substantial negative longitudinal magnetization to the spins located in the planner section, and step d) includes the step of subtracting the two resulting image data sets.

7. The image as recited in claim 1 in which the imaging pulse sequence performed in step b) includes applying a magnetic field gradient pulse to produce a phase roll in the NMR signals produced by spins disposed along the direction of projection in step d).

8. The method as recited in claim 1 in which the imaging pulse sequence includes a bipolar velocity encoding gradient and the reconstructed image indicates the velocity of spins in the object.

9. The method as recited in claim 1 in which the moving object moves as a result of a beating heart in a subject being imaged, said method further including:
   producing, prior to step a), a cardiac gating signal to indicate a reference cardiac phase;
   performing step a) at a first selected cardiac phase relative to the reference cardiac phase when the object is located in the selected region; and
   performing step b) at a second selected cardiac phase relative to the reference cardiac phase when the object has moved to another location.

10. The method as recited in claim 9 in which the object is a coronary artery on the beating heart.

11. The method as recited in claim 10 including the step of introducing a contrast agent into the coronary artery before performing steps a) and b).

12. The method as recited in claim 6 in which the moving object is a coronary artery on a beating heart, said method further including:
   producing, prior to step a), a cardiac gating signal to indicate a reference cardiac phase;
   performing step a) at a first selected cardiac phase relative to the reference cardiac phase when the coronary artery is located in the selected region; and
   performing step b) at a second selected cardiac phase relative to the reference cardiac phase when the coronary artery has moved to another location at which a portion of the coronary artery is outside of said selected region.

13. The method as recited in claim 12 in which the size of said volume is determined by the extent of the movement of the coronary artery during the heart beat, such that the coronary artery (206) remains in the volume during the entire heart beat.

14. The method as recited in claim 1 in which the step of performing a two-dimensional imaging pulse sequence includes the steps of:
   i) applying a first magnetic field gradient oriented along a projection axis;
   ii) applying a phase encoding magnetic field gradient oriented along a phase encoding axis orthogonal to the projection axis, and
   iii) applying a readout magnetic field gradient orthogonal to the projection axis and the phase encoding axis.

15. The method as recited in claim 1 in which the imaging pulse sequence comprises an echo planer imaging (EPI) pulse sequence.

16. The method as recited in claim 9, further including the step of suppressing NMR signals produced by spins in the myocardium.

17. The method as recited in claim 16 wherein the step of suppressing NMR signals produced by spins in the myocarium comprises generating a magnetization transfer pulse as part of a preparatory pulse sequence.

18. The method as recited in claim 1 in which the moving object is a blood vessel in a human subject, said method further including the step of introducing a contrast agent into the blood vessel to enhance the NMR signals produced by spins in the blood vessel.

19. An MRI system for producing a two-dimensional image of a moving object comprising:
   a magnet assembly for producing a polarizing magnetic field in a volume that contains the moving object;
   a physiological acquisition controller for detecting presence of the moving object in a selected region of said volume;
   an RF coil for producing transverse magnetization in spins located in said volume but outside of said selected region such that longitudinal magnetization of said spins is substantially altered when the moving object is in said selected region, said RF coil being adapted to receive an imaging pulse sequence which includes:
      a) selective RF excitation pulse for producing transverse magnetization in spins located throughout said volume;

b) a negative, z-axis gradient pulse for rephasing the transverse magnetization throughout the volume;

c) a transceiver for acquiring NMR signalsproduced by the transverse magnetization; and d) a system control for reconstructing a two-dimensional image from the acquired NMR signals which is a projection from said volume along a projection axis.

20. The MRI system as recited in claim 19 in which said RF coil includes:

e) a gradient coil assembly and magnetic field gradient amplifiers coupled thereto for producing a magnetic field gradient directed along said projection axis after the selective RF excitation pulse produces the transverse magnetization to limit coherent addition of signals from said volume that includes said selected region.

21. The MRI system as recited in claim 19 wherein said gradient coil assembly and said magnetic field gradient amplifiers are adapted to produce magnetic field gradients after the selective RF excitation pulse produces said transverse magnetization to dephase said transverse magnetization and to thereby suppress any NMR signals that said transverse magnetization may produce during the acquisition of NMR signals.

22. The MRI system as recited in claim 19 wherein said gradient coil assembly and said magnetic field gradient amplifiers are adapted to produce a bipolar magnetic field gradient for velocity encoding the transverse magnetization produced by the selective RF excitation pulse.

23. A method for producing an image of an object that moves within a volume, comprising the steps of:

a) producing a polarizing magnetic field in the volume;

b) performing a preparation pulse sequence to produce an RF excitation field and a magnetic field gradient for altering longitudinal magnetization of spins in the volume differently than longitudinal magnetization of spins that form a selected part of the object, the preparation pulse sequence including:

i) generating a non-selective RF excitation pulse to produce transverse magnetization in spins located throughout the volume, said non-selective RF excitation pulse having a flip angle of plus (90+α) degrees;

ii) generating a selective RF excitation pulse in the presence of a slice select magnetic field gradient pulse to re-establish longitudinal magnetization in the spins forming the selected part of the object, said selective RF excitation pulse having a flip angle of minus (90+α) degrees; and iii) at a subsequent time, applying a selective RF excitation pulse to produce transverse magnetization in said spins located throughout the volume;

c) producing transverse magnetization in spins that form the selected part of the object d) acquiring NMR signals produced by spins undergoing said transverse magnetization in the presence of a readout magnetic field gradient; and e) reconstructing a projection image of the object using the acquired NMR signals.

24. The method as recited in claim 23 in which the preparation pulse sequence further includes:

iv) applying a magnetic field spoiler gradient after step ii) to dephase residual transverse magnetization in spins throughout the volume.

* * * * *